US010617695B2

(12) United States Patent
Ingerman et al.

(10) Patent No.: US 10,617,695 B2
(45) Date of Patent: *Apr. 14, 2020

(54) OPHTHALMIC COMPOSITIONS CONTAINING ALCAFTADINE

(71) Applicant: Vistakon Pharmaceuticals, LLC, Jacksonville, FL (US)

(72) Inventors: Avner Ingerman, Bellmead, NJ (US); Frans Janssens, Bonheiden (BE); Anton Megens, Beerse (BE); Mark B. Abelson, Andover, MA (US)

(73) Assignee: Vistakon Pharmaceuticals, LLC, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/267,645

(22) Filed: Sep. 16, 2016

(65) Prior Publication Data

US 2017/0065605 A1    Mar. 9, 2017

Related U.S. Application Data

(60) Division of application No. 14/049,078, filed on Oct. 8, 2013, now abandoned, which is a continuation of application No. 13/020,961, filed on Feb. 4, 2011, now abandoned, which is a continuation of application No. 11/690,954, filed on Mar. 26, 2007, now Pat. No. 8,664,215, which is a continuation-in-part of application No. 11/688,016, filed on Mar. 19, 2007, now abandoned.

(60) Provisional application No. 60/788,185, filed on Mar. 31, 2006.

(51) Int. Cl.
*A61K 31/55* (2006.01)
*A61K 9/00* (2006.01)
*A61K 9/08* (2006.01)

(52) U.S. Cl.
CPC ............ *A61K 31/55* (2013.01); *A61K 9/0048* (2013.01); *A61K 9/08* (2013.01)

(58) Field of Classification Search
CPC ......... A61K 31/55; A61K 9/08; A61K 9/0048
See application file for complete search history.

(56) References Cited

U.S. PATENT DOCUMENTS

| 4,503,060 A | 3/1985 | Walther et al. |
| 5,008,268 A | 4/1991 | Janssens et al. |
| 5,468,743 A | 11/1995 | Janssens et al. |
| 5,641,805 A | 6/1997 | Hayakawa et al. |
| 8,664,215 B2 | 3/2014 | Parasrampuria et al. |
| 2006/0100408 A1 | 5/2006 | Powell et al. |
| 2007/0077302 A1* | 4/2007 | Alli ...................... A61K 31/335 424/486 |
| 2007/0077303 A1 | 4/2007 | Alli et al. |
| 2007/0265234 A1 | 11/2007 | Mahadevan et al. |
| 2008/0051385 A1 | 2/2008 | Parasrampuria et al. |

FOREIGN PATENT DOCUMENTS

| AU | 2006225171 | 4/2007 |
| EP | 0000716 | 2/1979 |
| EP | 0073506 | 3/1983 |
| EP | 0517160 | 6/1992 |
| EP | 0518435 | 12/1992 |
| EP | 1774961 | 4/2007 |
| WO | 199206981 | 4/1992 |
| WO | 9222551 | 12/1992 |
| WO | 2007117971 | 3/2007 |

OTHER PUBLICATIONS

Nevitt; "Clinical Review: NDS 22-134: (alcaftadine ophthalmic solution) 0.25%"; 2009; https://www.accessdata.fda.gov/drugsatfda_docs/pediatric/22134_alcaftadine_clinical_PREA.pdf (Year: 2009).*
Awouters, Fran et al., Interaction of Astemizole and Other Drugs with Passive Cutaneous Anaphylactic and Histamine-, Serotonin-, and Compound 48/80-Induced Skin Reactions in the Rat: A Procedure to Determine Anti-Allergic Effectiveness, Drug Develop. Res., 1985, 137-145, 5.
Awouters, Fran et al., Oral Antiallergic Activity in Ascaris Hypersensitive Dogs: A Study of Known Antihistamines and of the New Compounds Ramastine (R 57 959) and Levocabastine (R 50 547), Drug Develop. Res., 1986, 95-102, 8.
Berdy, Gregg et al., Allergic Conjunctivitis: A Survey of New Antihistamines, Journal of Ocular Pharmacology, 1991, 313-324, 7 (4).
Bhargava, A. et al., Ocular Allergic Disease, Drugs of Today/ Medicantos de Actualidad, Drugs of Today, 1998, 957-971, 34 (11).
D'Arienzo, PA et al., Clinical Efficacy of Olopatadine and Epinastine in Allergic Conjunctivitis Subjects Defined by Sensitivity to Conjunctival Allergen Challenge (CAC), IVOS, 2005, 2677, 46: E-Astract.
Evaluation of Efficacy of Ophthalmic Solution in Induced Acute Allergic Conjunctivitis, ClinicalTrials.gov, Sep. 13, 2009, 2 pages, NA.

(Continued)

*Primary Examiner* — Timothy P Thomas
(74) *Attorney, Agent, or Firm* — Lorenz Siddiqi

(57) ABSTRACT

Compositions, kits and methods for the treatment or prevention of ocular allergies and inflammation and the symptoms thereof containing alcaftadine or a pharmaceutically acceptable salt thereof.

20 Claims, No Drawings

(56) References Cited

OTHER PUBLICATIONS

Niemegeers, CJE et al., Protection of Rats from Compound 48/80-Induced Lethality: A Simple Test for Inhibitors of Mast Cell-Mediated Shock, Arch. Int. Pharmacodyn., 1978, 164-176, 234.
Ono, Santa Jeremy et al., Allergic Conjunctivitis: Update on Pathophysiology and Prospects for Future Treatment, J. Allergy Clin. Immuno, 2005, 118-122, 115 (1).
Safety Study of Ophthalmic Solutions in Healthy, Normal Volunteers, ClinicalTrials.gov, Sep. 13, 2009, 3 pages, N/A.
STN: Alcaftadine; Registry file RN 147084-10-4; entered STN 1993; printed Oct. 27, 2009.
Unknown, Prevent—Definition from Merriam-Webster Online Dictionary, Merriam-Webster Online Dictionary, Oct. 27, 2009, 2 pages, N/A.
USP Dictionary of USAN and International Drug Names: 2006 USP Dictionary Supplement 3, Pharmacopeial Forum 32(5): 1598 (2006).
Van Wauwe, J. et al., In Vivo Pharmacology of Astemizole, a New Type of H1-Antihistaminic Compound, Arch. Int. Pharmacodyn., 1981, 39-51, 251.
Sklubalova, Z. et al., Systematic study of factors affecting eye drop size and dosing variablity, Die Pharmazie: An International Journal of Pharmaceutical Sciences, 2005, 917-921, 60.
Le Hir, A., Via Ophtalmic Eye Drops, Galenic Pharmacy, 1995, 344-352.
Lehman, J., et al., Selecting the Optimal Oral Antihistamine for Patients with Allergic Rhinitis, Drugs, 2006, 2309-2319, 66 (18).

* cited by examiner

OPHTHALMIC COMPOSITIONS CONTAINING ALCAFTADINE

RELATED APPLICATION

This application is a divisional of U.S. patent application Ser. No. 14/049,078, filed Oct. 8, 2013, which is a continuation of U.S. patent application Ser. No. 13/020,961, filed Feb. 4, 2012, now abandoned, which is a continuation of U.S. patent application Ser. No. 11/690,954, filed Mar. 26, 2007, now U.S. Pat. No. 8,664,215, issued Mar. 4, 2014, which is a continuation-in-part application of U.S. patent application Ser. No. 11/688,016, filed Mar. 19, 2007, now abandoned, which claims the benefit of U.S. Provisional Patent Application 60/788,185, filed on Mar. 31, 2006, the disclosures of which are hereby incorporated by reference in their entireties and serve as the basis of a priority and/or benefit claim for the present application.

FIELD OF THE INVENTION

This invention is directed to the treatment or prevention of ocular conditions. More specifically, the invention is directed to compositions of alcaftadine or 6,11-dihydro-11-(1-methyl-4-piperdinylidene)-5H-imidazo[2,1-b][3]benazepine-3-carboxylic acid, as well as methods for using such compositions for the treatment or prevention of ocular inflammation and allergies.

BACKGROUND

Allergic disorders of the ocular surface include a wide variety of pathological conditions including Seasonal Allergic Conjunctivitis ("SAC"), Perennial Allergic Conjunctivitis ("PAC"), Vernal Keratoconjunctivitis and Atopic Keratoconjunctivitis. It is estimated that over 20% of the general population suffer from some form of ocular allergy. Of those, approximately 90% suffer from either SAC, PAC or both.

The ocular allergic reaction is an IgE-dependent (Type I) hypersensitivity inflammatory response that most commonly affects adults between 20 and 40 years of age. In susceptible individuals, initial exposure of allergen to the ocular surface stimulates the production of allergen specific immunologic antibodies (IgE). IgE then binds to the membrane bound Fc.epsilon.R-1 receptor of naive mast cells in the ocular mucosa. The mast cell is a granulocyte, containing a number of preformed mediators, including histamine and proteoglycans. Once the mast cell is activated, newly formed chemical mediators are formed, which include prostaglandin D2, leukotrienes, and platelet aggregating factor. Subsequent exposure of allergen to the IgE coated mast cells leads to the release of preformed, as well as newly formed, mediators contained within the granules of the mast cell.

The clinical symptoms of allergic conjunctivitis include itching, redness, swelling of the eyelid, chemosis and tearing. Histamine is the primary mediator in the allergic response. After mast cell degranulation, histamine binds to receptors located in the conjunctiva. The binding of histamine to H1 receptors on nerve cells induces itching. Activation of H1 and H2 receptors on the vaso-endothelium induces vasodilatation and increases vascular permeability facilitating the migration of inflammatory mediators, such as IL-1$\alpha$ and IL-1$\beta$, into the blood vessel and the subsequent recruitment of leukocytes into the conjunctival tissue. Activation of the histamine receptors leads to ocular hyperemia, chemosis, lid swelling and exudation of fluid from blood vessels into the surrounding tissue, which in turn causes inflammation. The chemotaxis of leukocytes such as eosinophils and neutrophils into the conjunctival tissue in turn leads to further tissue damage.

Historically, antihistamines have been the mainstay for treatment of ocular allergic disease. These therapies vary in potency, specificity and duration of action. First generation anti-histamines such as pheniramine and antazoline are known for their rapid onset of action. Unfortunately, these compounds also cause ocular discomfort and their efficacy diminishes after only a few hours. Second-generation H1 antagonists such as levocabastine and emadastine present less ocular discomfort and have a somewhat longer duration of action. However, these compounds have limited anti-inflammatory effects, and do little to inhibit the late-phase components of the inflammatory response.

Currently, the most effective therapies for the management of ocular allergy are drugs such as olopatadine, ketotifen and azelastine, which have both anti-histaminic and mast cell stabilizing properties. These therapies are generally well tolerated and their effects can last up to 8 to 12 hours. Although reported to be superior to compounds that effect only a single component of the allergic response, these compounds often fail to provide relief more than one ocular allergy symptoms.

A drug's affect on ocular redness, chemosis and eyelid swelling offers a significant improvement over existing therapies. Additionally, since the majority of newer ophthalmic anti-allergic agents have limited durations of action, twice daily dosing is required. A topical preparation with a longer duration of action will be advantageous because it may be instilled once daily. Thus, new therapies that can offer advantages in areas such as efficacy and duration of action, while offering similar safety profiles, are needed. The instant invention is directed to these and other objectives.

DETAILED DESCRIPTION OF THE INVENTION

The invention includes methods of treating or preventing ocular allergy by administering alcaftadine to the eye of a patient. The inventions described herein are based at least in part on the surprising discovery that alcaftadine treats or prevents a number of different symptoms of ocular allergy that make it especially useful for the treatment or prevention of ocular allergy. The methods, ophthalmic compositions, and kits of the present invention alleviate clinical symptoms of ocular allergy and ocular inflammation with minimal systemic absorption of the active drug. This unusual combination of properties, together with an excellent safety profile and tolerability when formulated for topical administration to the eye, makes the drug especially useful for the treatment or prevention of ocular allergy. Specifically, the invention includes a method of treating or preventing a clinical symptom of ocular allergy, comprising administering to the eye of a patient an effective amount of alcaftadine, its pharmaceutically acceptable salts, its N-oxides, hydrates, solvates, polymorphs, pro-drugs, or mixtures thereof.

Alcaftadine, also known by the chemical name 6,11-dihydro-11-(1-methyl-4-piperidinylidene)-5H-imidazo[2,1-b][3]benzazepine-3-carboxaldehyde, has the following chemical formula:

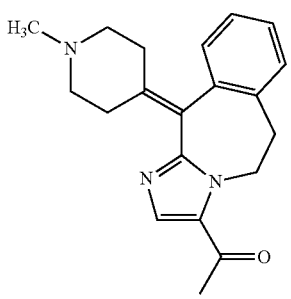

Formula I

The compound and methods for its preparation are disclosed in U.S. Pat. No. 5,468,743, which is incorporated herein by reference in its entirety for all purposes. The preferred methods and ophthalmic compositions of the invention contain the alcaftadine compound of Formula I, but may alternatively be present as an alcaftadine salt. Pharmaceutically acceptable salts of alcaftadine can be formed from organic and inorganic acids. Suitable acids include, but are not limited to, acetic, 4-acetamido benzoic acid, benzenesulfonic, camphorsulfonic, citric, 2,3:4,6-di-O-isopropylidene-2-keto-L-gulonic acid monohydrate, formic, fumaric, hydrochloric, hydrobromic, lactic, maleic, L-(−)malic, malic, malonic, mandelic, methanesulfonic, naphthalenesulfonic, nitric, oxalic, phthalic, phosphoric, propionic, DL-pyroglutamic, saccharin, salicyclic, succinic, sulfuric, tartaric, trifluoro acetic, L-(+)tartaric, and toluenesulfonic acids.

As used herein the terms "ocular allergy" refers to an allergic disorder of the ocular surface caused by pathogenic allergens. Allergic conjunctivitis is the preferred ocular allergy and includes a wide variety of pathological conditions including Seasonal Allergic Conjunctivitis ("SAC"), Perennial Allergic Conjunctivitis ("PAC"), Vernal Keratoconjunctivitis and Atopic Keratoconjunctivitis.

"Clinical symptoms" of ocular allergy include but are not limited to ocular itching, ocular redness, swelling of the eyelids, chemosis, tearing, and nasal inflammation, nasal congestion, rhinorrhea, nasal pruritis and ear/palate pruritis, and sneezing. It is preferred that the methods of the invention treat or prevent at least two clinical symptoms, more preferably at least three, even more preferably more that four. For example, the methods of the invention treat or prevent at least one of the following clinical symptoms associated with allergic conjunctivitis ocular itching, ocular redness, chemosis, tearing, swelling of lid nasal congestion, or rhinorrhea. Preferably the methods of the invention treat or prevent, ocular itching and ocular redness; treat or prevent ocular itching, ocular redness, and chemosis; treat or prevent ocular itching, ocular redness, chemosis, and tearing; treat or prevent ocular itching, ocular redness, chemosis, tearing, and swelling of the lid; treat or prevent ocular itching, ocular redness, chemosis, tearing, swelling of the lid, and nasal congestion; treat or prevent ocular itching, ocular redness, chemosis, tearing, swelling of the lid, nasal congestion, and rhinorrhea; treat or prevent nasal congestion and rhinorrhea.

The term "patient," as used herein, refers to animals, including mammals, preferably humans. The "effective amount" of alcaftadine, its pharmaceutically acceptable salts, its N-oxides, hydrates, solvates, polymorphs, pro-drugs, or mixtures thereof, is the amount the substance required to treat or prevent the symptoms of ocular allergy. The effective amount may vary from patient to patient depending upon the ability of alcaftadine, its pharmaceutically acceptable salts, its N-oxides, hydrates, solvates, polymorphs, pro-drugs, or mixtures thereof, alone or in combination with one or more combination drugs to elicit a desired response in the patient. Other factors determining the effective amount will include, but are not limited to the disease state or severity of the condition to be alleviated, hormone levels, age, sex, weight of the patient, the state of being of the patient, and the severity of the pathological condition being treated, concurrent medication or special diets then being followed by the particular patient, and other factors which those ordinarily skilled in the art will recognize, with the appropriate dosage ultimately being at the discretion of the attending physician. Dosage regimens may be adjusted to provide the improved therapeutic response. An effective amount is also one in which any toxic or detrimental effects of the components are outweighed by the therapeutically beneficial effects. It is preferred that for most patients a 50 µL drop of a 0.25% ocular solution contains 0.125 mg of alcaftadine. Assuming that 100% of drug is systemically absorbed, a 70 kg person, using the eye drops bilaterally, meaning in each eye, once daily, would be exposed to a dose of 0.25 mg/d, or 3.57 µg/kg per day. It is reasonable to assume that the actual systemic exposure will be lower, since it is likely that not all of the amount will be absorbed. It is preferred that the effective amount of alcaftadine, its pharmaceutically acceptable salts, its N-oxides, hydrates, solvates, polymorphs, pro-drugs, or mixtures thereof, is between less than about 0.25 mg and greater than or equal to about 0.015 mg, more preferably, between about 0.030 mg and about 0.14 mg, more preferably between about 0.075 mg and about 0.125 mg.

The term "pharmaceutically acceptable" as used herein refers to materials that are generally not toxic or injurious to a patient when used with alcaftadine, its pharmaceutically acceptable salts, its N-oxides, hydrates, solvates, polymorphs, pro-drugs, or mixtures thereof, the present invention, including when the alcaftadine, its pharmaceutically acceptable salts, its N-oxides, hydrates, solvates, polymorphs, pro-drugs, or mixtures thereof, is formulated as ophthalmic compositions, as defined herein.

Alcaftadine, its pharmaceutically acceptable salts, its N-oxides, hydrates, solvates, polymorphs, pro-drugs, or mixtures thereof, may be administered to the patient by any route of administration capable of delivering the drug to the eye of the patient, in any pharmaceutically acceptable dosage form. Thus, the drug may be administered to the patient in the form of an ophthalmic composition, as defined herein, or any other formulation, device or mechanism suitable for the short term or long term delivery of an effective amount of the drug to the patient's eye. The drug may be administered to the patient in an ophthalmic inserts containing or coated with alcaftadine, its pharmaceutically acceptable salts, its N-oxides, hydrates, solvates, polymorphs, pro-drugs, or mixtures thereof, including but not limited to contact lenses, punctal plugs, or, ocular inserts. In preferred methods of the present invention, the drug is administered topically in the form of an ophthalmic composition selected from the group consisting of ophthalmic solutions or suspensions (i.e., eye drops), ophthalmic ointments, or ophthalmic gels.

Further, the invention includes a method of treating or preventing a clinical symptom of ocular inflammation, comprising administering to the eye of a patient an effective amount of alcaftadine, its pharmaceutically acceptable salts, its N-oxides, hydrates, solvates, polymorphs, pro-drugs, or mixtures thereof. The terms alcaftadine, clinical symptom, patient, pharmaceutically acceptable, pharmaceutically acceptable salts, and effective amount all have their aforementioned meanings and preferred ranges. The term ocular inflammation refers to inflammation of any part of the anterior portion of the eye. Such ocular inflammation may be caused by any of the following or any combination of the following dry eye, contact lens wear, bacterial infections, fungal infections, or viral infections. The preferred causes of ocular inflammation are bacterial infections or viral infections.

In addition the invention includes a method of treating or preventing a mechanistic symptom associated with ocular allergy or ocular inflammation comprising administering to the eye of a patient an effective amount of alcaftadine, its pharmaceutically acceptable salts, its N-oxides, hydrates, solvates, polymorphs, pro-drugs, or mixtures thereof. The terms alcaftadine, patient pharmaceutically acceptable, pharmaceutically acceptable salts, effective amount, ocular allergy, and ocular inflammation all have their aforementioned meanings and preferred ranges. "Mechanistic symptoms" are cellular reactions that either elicit or suppress symptoms of a disease state such as ocular allergy or ocular inflammation. Mechanistic symptoms include but are not limited to vascular leakage, a reduction in the integrity of the conjunctival epithelial tight junctions, modulation of the $H_4$ receptor, and mast cell degradation. The preferred methods of the invention treat or prevent at least two mechanistic symptoms, more preferably treat or prevent at least three mechanistic symptoms, even more preferably treat or prevent at least four mechanistic symptoms. For example the preferred methods treat or prevent vascular leakage, and a reduction in the integrity of the conjunctival epithelial tight; treat or prevent vascular leakage, a reduction in the integrity of the conjunctival epithelial tight junctions, and modulation of the $H_4$ receptor; treat or prevent vascular leakage, a reduction in the integrity of the conjunctival epithelial tight junctions, modulation of the $H_4$ receptor, and mast cell degradation.

Further still, the invention includes a method of treating or preventing a nasal symptom of ocular allergy, comprising administering to the nose of a patient an effective amount of alcaftadine, its pharmaceutically acceptable salts, its N-oxides, hydrates, solvates, polymorphs, pro-drugs, or mixtures thereof. The terms alcaftadine, patient, pharmaceutically acceptable, pharmaceutically acceptable salts, ocular allergy, and effective amount all have their aforementioned meanings and preferred ranges. "Nasal symptoms" of allergy are a subset of clinical symptoms as defined above and include nasal inflammation, nasal congestion, rhinorrhea, nasal pruritis, and sneezing. The preferred nasal symptoms are rhinorrhea and nasal congestion.

Alfcaftadine may be administered to the patient in the form of an ophthalmic composition, as defined herein, or any other formulation, device or mechanism suitable for the short term or long term delivery of an effective amount of the drug to the patient's nose, preferably the patient's nostrils. In the preferred methods of the present invention, alcaftadine, its pharmaceutically acceptable salts, its N-oxides, hydrates, solvates, polymorphs, pro-drugs, or mixtures thereof, is administered to the patient's nostrils topically in the form of an ophthalmic composition selected from the group consisting of ophthalmic solutions or suspensions (i.e., nasal drops and spray), ophthalmic ointments, or ophthalmic gels (as defined herein).

Further the invention includes a method of treating or preventing a clinical symptom of ocular allergy, comprising administering to the eye of a patient an ophthalmic composition comprising alcaftadine, its pharmaceutically acceptable salts, its N-oxides, hydrates, solvates, polymorphs, pro-drugs, or mixtures thereof. The terms alcaftadine, clinical symptom, ocular allergy, patient, pharmaceutically acceptable, and pharmaceutically acceptable salts, all have their aforementioned meanings and preferred ranges.

As used herein the term "ophthalmic composition" refers to any pharmaceutically acceptable formulation, delivery device, mechanism or system suitable for administration to the eye. The term "ophthalmic compositions" includes but are not limited to solutions, suspensions, gels, ointments, contact lenses, implants, sprays, depots or any other type of formulation, device or mechanism suitable for short term or long term delivery of alcaftadine, its pharmaceutically acceptable salts, its N-oxides, hydrates, solvates, polymorphs, pro-drugs, or mixtures thereof, to the eye. In contrast to oral or injectable formulations, ophthalmic compositions exhibit specific technical characteristics associated with their application to the eyes, including the use of pharmaceutically acceptable ophthalmic vehicles that avoid inducing various reactions such as, for example, irritation of the conjunctiva and cornea, closure of the eyelids, secretion of tears and painful reactions. Preferred ophthalmic compositions according to the invention are advantageously in the form of ophthalmic solutions or suspensions (i.e., eye drops), ophthalmic ointments, or ophthalmic gels containing alcaftadine, its pharmaceutically acceptable salts, its N-oxides, hydrates, solvates, polymorphs, pro-drugs, or mixtures thereof. Depending upon the particular form selected, the compositions may contain various additives such as buffering agents, isotonizing agents, solubilizers, preservatives, viscosity-increasing agents, chelating agents, antioxidizing agents, and pH regulators.

Examples of suitable preservatives include, but are not limited to chlorobutanol, sodium dehydroacetate, benzalkonium chloride, cetyl pyridinium chloride, phenethyl alcohol, parahydroxybenzoic acid esters, and benzethonium chloride. The viscosity-increasing agents may be selected, for example, from methylcellulose, hydroxyethylcellulose, carboxymethylcellulose, hydroxypropylmethylcellulose, polyvinyl alcohol, carboxymethylcellulose, chondroitin sulfate, and salts thereof. Suitable solubilizers include, but are not limited to, polyoxyethylene hydrogenated castor oil, polyethylene glycol, polysorbate 80, and polyoxyethylene monostearate. Typical chelating agents include, but are not limited to, sodium edetate citric acid, stabilizing agents as defined in U.S. App. Pat. No. 60/783,557 filed on, Mar. 17, 2006, entitled "Methods for Stabilizing Oxidatively Unstable Pharmaceutical Compositions" and its corresponding non-provisional filing which are hereby incorporated by reference in their entirety. The stabilizers include, but are not limited to for example, sodium edetate and sodium hydrogen sulfite.

Useful pH regulators are commonly selected, for example, from sodium hydroxide, potassium hydroxide, sodium carbonate, citric acid, phosphoric acid, acetic acid, and hydrochloric acid. The pH of the ophthalmic compositions may range from about 5 to about 8, more preferably from about 6.5 to about 7.5. Even more preferably, the pH of the ophthalmic compositions is about 7.0. Useful buffers include, but are not limited to borate buffers, phosphate buffers, carbonate buffers, and acetate buffers. The concentration of buffer in the ophthalmic compositions may vary from about 1 mM to about 150 mM or more, depending on the particular buffer chosen. Preferably, the concentration of buffer is less than 100, more preferably from about 1 mM to about 25 mM, with a concentration of about 1 mM to about 20 mM more preferred.

As used herein, the term "vehicle" is intended to include any carrier, diluent or excipient suitable for ophthalmic use. "Excipient" refers to an ingredient that provides one or more of bulk, imparts satisfactory processing characteristics, helps control the dissolution rate, and otherwise gives additional desirable characteristics to the compositions. Included within this term, inter alia, are compounds well known to those of ordinary skill in the art, as described, for example, in the Handbook of Pharmaceutical Excipients, (American Pharmaceutical Association, Washington, D.C. and Pharmaceutical Press, London, England, 4$^{th}$ ed. 2003), incorporated herein by reference in its entirety. In particular, the excipients are selected such that the ophthalmic composition does not trigger a secretion of tears that will entrain the active ingredient. Acceptable excipients are well known to a person skilled in the art, who will know how to select them depending on the desired formulation.

When concentrations, amounts, percentages, and other numerical data are expressed or presented herein in a range format, it is to be understood that such a range format is used merely for convenience and brevity and thus are to be interpreted flexibly to include not only the numerical values explicitly recited as the limits of the range, but also to include each of the individual numerical values or sub-ranges encompassed within that range as if each numerical value and sub-range is explicitly recited. As an illustration, a concentration range of "about 1 weight % to about 10 weight %" is to be interpreted to include not only the explicitly recited concentration of about 1 weight % to about 10 weight %, but also individual concentrations and the sub-ranges within the indicated range. Thus, included in this numerical range are individual concentrations such as 2 weight %, 5 weight %, and 8 weight %, and sub-ranges such as from 1 weight % to 3 weight %, from 5 weight % to 9 weight % and so forth. As used herein, the term "about" means plus or minus approximately ten percent of the indicated value, such that "about 50% by weight" indicates approximately 45% to 55% by weight.

Typically, the concentration of alcaftadine in the ophthalmic compositions of the present invention will be from about 0.005% by weight to about 10.0% by weight, with concentrations of from about 0.005 to about 0.4% being preferred, and concentrations of about 0.1% to about 0.35% being particularly preferred. A 50 µL drop of a 0.25% ocular solution contains 0.125 mg of alcaftadine. Assuming that 100% of drug is systemically absorbed, a 70 kg person, using the eye drops bilaterally, meaning in each eye, once daily, would be exposed to a dose of 0.25 mg/d, or 3.57 µg/kg per day. It is reasonable to assume that the actual systemic exposure will be lower, since it is likely that not all of the amount will be absorbed.

Further, still the invention includes a method of treating or preventing a mechanistic symptom of ocular allergy, comprising administering to the eye of a patient an ophthalmic composition comprising alcaftadine, its pharmaceutically acceptable salts, its N-oxides, hydrates, solvates, polymorphs, pro-drugs, or mixtures thereof. The terms alcaftadine, mechanistic symptom, patient, pharmaceutically acceptable, and pharmaceutically acceptable salts, all have their aforementioned meanings and preferred ranges.

Still further, the invention includes a method of treating or preventing a clinical symptom of ocular inflammation, comprising administering to the eye of a patient an ophthalmic composition comprising alcaftadine, its pharmaceutically acceptable salts, its N-oxides, hydrates, solvates, polymorphs, pro-drugs, or mixtures thereof. The terms alcaftadine, clinical symptom, patient, pharmaceutically acceptable, and pharmaceutically acceptable salts, ocular inflammation, and ophthalmic composition all have their aforementioned meanings and preferred ranges.

Yet still further, the invention includes a method of treating or preventing a mechanistic symptom of ocular inflammation, comprising administering to the eye of a patient an ophthalmic composition comprising alcaftadine, its pharmaceutically acceptable salts, its N-oxides, hydrates, solvates, polymorphs, pro-drugs, or mixtures thereof. The terms alcaftadine, mechanistic symptom, patient, pharmaceutically acceptable, and pharmaceutically acceptable salts, ocular inflammation, ophthalmic composition all have their aforementioned meanings and preferred ranges.

Further, the invention includes an ophthalmic composition comprising alcaftadine, its pharmaceutically acceptable salts, its N-oxides, hydrates, solvates, polymorphs, pro-drugs, or mixtures thereof. The terms ophthalmic composition, alcaftadine, pharmaceutically acceptable salts all have their aforementioned meanings and preferred ranges. It is preferred that said ophthalmic composition further comprise a vehicle as defined herein.

Yet further still, the invention includes use of alcaftadine, its pharmaceutically acceptable salts, its N-oxides, solvates, polymorphs, pro-drugs, or mixtures thereof in the preparation of a medicament for the treatment or prevention of a clinical symptom of ocular allergy. The terms alcaftadine, clinical symptom, ocular allergy pharmaceutically acceptable salts all have their aforementioned meanings and preferred ranges Yet still further, the invention includes use of alcaftadine, its pharmaceutically acceptable salts, its N-oxides, hydrates, solvates, polymorphs, pro-drugs, or mixtures thereof in the preparation of a medicament for the treatment or prevention of a clinical symptom of ocular inflammation. The terms alcaftadine, clinical symptom, ocular inflammation pharmaceutically acceptable salts all have their aforementioned meanings and preferred ranges.

Yet further still, the invention includes use of alcaftadine, its pharmaceutically acceptable salts, its N-oxides, hydrates, solvates, polymorphs, pro-drugs, or mixtures thereof in the preparation of a medicament for the treatment or prevention of a mechanistic symptom of ocular allergy or ocular inflammation. The terms alcaftadine, mechanistic symptom, ocular allergy, ocular inflammation, pharmaceutically acceptable salts all have their aforementioned meanings and preferred ranges Still further, the invention includes a kit comprising an ophthalmic composition comprising alcaftadine, its pharmaceutically acceptable salts, its N-oxides, hydrates, solvates, polymorphs, pro-drugs, or mixtures thereof, contained within a container prepared from a pharmaceutically acceptable packaging material. The terms ophthalmic composition, alcaftadine, pharmaceutically acceptable salts all have their aforementioned meanings and preferred ranges. Pharmaceutically acceptable packaging materials include but are not limited to low density polyethylene ("LDPE"), high density polyethylene ("HDPE"), polypropylene, polystyrene, polycarbonate, polyesters (such as polyethylene terephthalate and polyethylene naphthalate), nylon, poly(vinyl chloride), poly(vinylidine chloride), poly(tetrafluoroethylene) and other materials known to those of ordinary skill in the art. Flexible bottles prepared from LDPE or HDPE are particularly preferred. Commercial sources of such materials include but are not limited to DuPont 20 Series specialty polyethylene, manufactured by DuPont, Tenite Polyethylene 1830F Natural, manufactured by Eastman Chemical Company, Purell 1840 Polyethylene, manufactured by Basell. The particularly preferred material is DUPONT™ 20-6064 (E. I. du Pont de Nemours and Company, Wilmington, Del.), a preferred LDPE packaging material, is commonly used for preparing flexible dropper bottles containing ophthalmic compositions by an injection blow molding process, and is approved for such use by the U.S. Food and Drug Administration. The kits may contain multiple doses of ophthalmic compositions containing alcaftadine or single use doses of alcaftadine.

Prior to filling, such bottles are routinely sterilized by gamma irradiation or with ethylene oxide gas, by methods widely known to those skilled in the art. Applicants have surprisingly found, however, that it is preferable to sterilize LDPE bottles with ethylene oxide gas, instead of with gamma radiation, as bottles sterilized with gamma radiation may exhibit decreased stability of the active ingredient.

6,11-dihydro-11-(1-methyl-4-piperdinylidene)-5H-imidazo[2,1-b][3]benazepine-3-carboxylic acid ("CAS #147083-93-0") has the following chemical formula

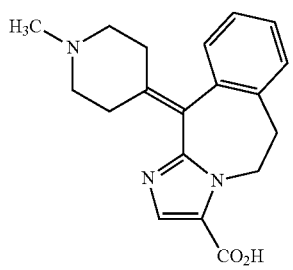

Formula II

The compound of Formula II was disclosed in U.S. Pat. No. 5,468,743. Preferred methods and ophthalmic compositions may contain Formula II as depicted, but Formula II may be present in the methods and ophthalmic compositions as its pharmaceutically acceptable salts, N-oxides, hydrates, solvates, polymorphs, pro-drugs, or mixtures thereof.

Specifically the invention includes a method of treating or preventing a clinical symptom of ocular allergy, comprising administering to the eye of a patient an effective amount of a compound of Formula II, its pharmaceutically acceptable salts, its N-oxides, hydrates, solvates, polymorphs, pro-drugs, or mixtures thereof. The terms a compound of Formula II, clinical symptom, ocular allergy, patient, pharmaceutically acceptable, and pharmaceutically acceptable salts, all have their aforementioned meanings and preferred ranges. The term "effective amount" of a compound of Formula II, its pharmaceutically acceptable salts, its N-oxides, hydrates, solvates, polymorphs, pro-drugs, or mixtures thereof is the amount of this substance required to treat or prevent the symptoms of ocular allergy. As described earlier in reference to the effective amount of alcaftadine, its pharmaceutically acceptable salts, its N-oxides, hydrates, solvates, polymorphs, pro-drugs, or mixtures thereof, the effective amount of a compound of Formula II, its pharmaceutically acceptable salts, its N-oxides, hydrates, solvates, polymorphs, pro-drugs, or mixtures thereof, may vary from patient to patient depending upon the ability of a compound of Formula II, its pharmaceutically acceptable salts, its N-oxides, hydrates, solvates, polymorphs, pro-drugs, and mixtures thereof, alone or in combination with one or more combination drugs to elicit a desired response in a patient.

Factors used to determine the effective amount are known to those of ordinary skill and some those factors are mentioned herein. It is preferred that the effect amount of a compound of Formula II is between less than about 0.25 mg and greater than or equal to about 0.015 mg, more preferably, between about 0.030 mg and about 0.14 mg, more preferably between about 0.075 mg and about 0.125 mg.

Further, the invention includes a method of treating or preventing a clinical symptom of ocular inflammation, comprising administering to the eye of a patient an effective amount of a compound of Formula II, its pharmaceutically acceptable salts, its N-oxides, hydrates, solvates, polymorphs, pro-drugs, or mixtures thereof. The terms a compound of Formula II, clinical symptom, ocular inflammation patient, pharmaceutically acceptable, pharmaceutically acceptable salts, and effective amount all have their aforementioned meanings and preferred ranges.

In addition the invention includes a method of treating or preventing a mechanistic symptom associated with ocular allergy or ocular inflammation comprising administering to the eye of a patient an effective amount of a compound of Formula II, its pharmaceutically acceptable salts, N-oxides, hydrates, solvates, polymorphs, pro-drugs, or mixtures thereof. The terms a compound of Formula II, patient pharmaceutically acceptable, pharmaceutically acceptable salts, effective amount, mechanistic symptoms, ocular allergy, and ocular inflammation all have their aforementioned meanings and preferred ranges.

Further still, the invention includes a method of treating or preventing a nasal symptom of ocular allergy, comprising administering to the nose of a patient an effective amount of a compound of Formula II, its pharmaceutically acceptable salts, its N-oxides, hydrates, solvates, polymorphs, pro-drugs, or mixtures thereof. The terms a compound of Formula II, patient, pharmaceutically acceptable, pharmaceutically acceptable salts, nasal symptoms, and effective amount all have their aforementioned meanings and preferred ranges.

Further the invention includes a method of treating or preventing a clinical symptom of ocular allergy, comprising administering to the eye of a patient an ophthalmic composition comprising a compound of Formula II, its pharmaceutically acceptable salts, its N-oxides, hydrates, solvates, polymorphs, pro-drugs, or mixtures thereof. The terms a compound of Formula II, clinical symptom, patient, ophthalmic composition, pharmaceutically acceptable, and pharmaceutically acceptable salts, all have their aforementioned meanings and preferred ranges.

Further, still the invention includes a method of treating or preventing a mechanistic symptom of ocular allergy, comprising administering to the eye of a patient an ophthalmic composition comprising a compound of Formula II, its pharmaceutically acceptable salts, its N-oxides, hydrates, solvates, polymorphs, pro-drugs, or mixtures thereof. The terms a compound of Formula II, mechanistic symptom, patient, pharmaceutically acceptable, and pharmaceutically acceptable salts, all have their aforementioned meanings and preferred ranges.

Still further, the invention includes a method of treating or preventing a clinical symptom of ocular inflammation, comprising administering to the eye of a patient an ophthalmic composition comprising a compound of Formula II, its pharmaceutically acceptable salts, its N-oxides, hydrates, solvates, polymorphs, pro-drugs, or mixtures thereof. The terms a compound of Formula II, clinical symptom, patient, pharmaceutically acceptable, and pharmaceutically acceptable salts, ocular inflammation, and ophthalmic composition all have their aforementioned meanings and preferred ranges.

Yet still further, the invention includes a method of treating or preventing a mechanistic symptom of ocular inflammation, comprising administering to the eye of a patient an ophthalmic composition comprising a compound of Formula II, its pharmaceutically acceptable salts, its N-oxides, hydrates, solvates, polymorphs, pro-drugs, or mixtures thereof. The terms a compound of Formula II, mechanistic symptom, patient, pharmaceutically acceptable, and pharmaceutically acceptable salts, ocular inflammation, ophthalmic composition all have their aforementioned meanings and preferred ranges.

Further, the invention includes an ophthalmic composition comprising a compound of Formula II, its pharmaceutically acceptable salts, its N-oxides, hydrates, solvates, polymorphs, pro-drugs, or mixtures thereof. The terms ophthalmic composition, a compound of Formula II, pharmaceutically acceptable salts all have their aforementioned meanings and preferred ranges. It is preferred that said ophthalmic composition further comprise a vehicle as defined herein.

Yet further still, the invention includes use of a compound of Formula II, its pharmaceutically acceptable salts, its N-oxides, hydrates, solvates, polymorphs, pro-drugs, or mixtures thereof in the preparation of a medicament for the treatment or prevention of a clinical symptom of ocular allergy. The terms a compound of Formula II, clinical symptom, ocular allergy pharmaceutically acceptable salts all have their aforementioned meanings and preferred ranges.

Yet still further, the invention includes use of a compound of Formula II, its pharmaceutically acceptable salts, its N-oxides, hydrates, solvates, polymorphs, pro-drugs, or mixtures thereof in the preparation of a medicament for the treatment or prevention of a clinical symptom of ocular inflammation. The terms a compound of Formula II, clinical symptom, ocular inflammation pharmaceutically acceptable salts all have their aforementioned meanings and preferred ranges.

Yet further still, the invention includes use of a compound of Formula II, its pharmaceutically acceptable salts, its N-oxides, hydrates, solvates, polymorphs, pro-drugs, or mixtures thereof in the preparation of a medicament for the treatment or prevention of a mechanistic symptom of ocular allergy or ocular inflammation. The terms a compound of Formula II, mechanistic symptom, ocular allergy, ocular inflammation, pharmaceutically acceptable salts all have their aforementioned meanings and preferred ranges.

Still further, the invention includes a kit comprising an ophthalmic composition comprising a compound of Formula II, its pharmaceutically acceptable salts, its N-oxides, hydrates, solvates, polymorphs, pro-drugs, or mixtures thereof contained within a container prepared from a pharmaceutically acceptable packaging material. The terms ophthalmic composition, alcaftadine, pharmaceutically acceptable salts and pharmaceutically acceptable packaging material, all have their aforementioned meanings and preferred ranges.

EXAMPLES

The invention is further demonstrated in the following examples. The examples are for purposes of illustration and are not intended to limit the scope of the present invention.

Example 1

Alcaftadine Ophthalmic Solutions

Ophthalmic solutions containing alcaftadine were prepared in accordance with Table I. To assure sterility, the solutions were passed through 0.22 micron sterilizing filter prior to being filled into LDPE bottles that had previously undergone ethylene oxide sterilization.

TABLE 1

| Ingredient | Conc. mg/mL | Conc. mg/mL | Conc. mg/mL |
| --- | --- | --- | --- |
| Alcaftadine | 1.0 | 2.5 | 5.0 |
| Dibasic sodium phosphate USP | 11.1 | 11.1 | 11.1 |
| Monobasic potassium phosphate NF | 5.1 | 5.3 | 5.6 |
| Sodium chloride USP | 2.4 | 2.3 | 2.1 |
| Benzalkonium chloride NF | 0.2 | 0.2 | 0.2 |
| Edetate disodium USP | 1.1 | 1.1 | 1.1 |
| Purified water USP | Q.S. | Q.S. | Q.S. |

Example 2

Anti-Allergic Activity

The effect of alcaftadine against acute-phase reactions of allergic conjunctivitis (edema and erythema) was compared to the effect of other known anti-allergens in guinea pigs that were systemically sensitized to rabbit skin squames and topically challenged 17 days later with rabbit allergens.

Anesthetized male albino guinea pigs (Dunkin-Hartley) weighing about 230 to 250 g were injected intramuscularly at the left quadriceps with 50 µl of purified rabbit allergens. The rabbit allergens consisted of $Al(OH)_3$-adsorbed rabbit squames (Halab, Brussels, Belgium), which had been homogenized and washed clean of preservative (0.5% (V/V) phenol) with sterile physiologic saline.

Alcaftadine was orally administered to each eye in dosages ranging from 0.005 mg/kg to 1.0 mg/kg at 24 hours and 1 hour before challenge. Other test compounds included oxatomide, ketotifen, astemizole, cetirizine, loratadine and terfenadine, administered at dosages of 0.1 mg/kg and 1.0 mg/kg.

At day 17 post sensitization the left eye was challenged by instilling 25 µl of 100% normal rabbit serum. At the same time as the allergen challenge, the right eye was instilled with 25 µl of 1.5 mg/ml histamine dihydrochloride (98%, Sigma) dissolved in deionised, Millipore-filtered water.

Thirty minutes after challenge, edema and erythema were assessed in the tarsal and bulbar conjunctiva of both eyes and scored as absent (0), weak (1), moderate (2), severe (3), or very severe (4) by a trained technician. Alcaftadine significantly alleviated the acute allergic symptoms beginning at doses of 0.1 mg/kg. In this test, alcaftadine was found to be more potent (on an equivalent mg/kg basis) than oxatomide, ketotifen and terfenadine and significantly more potent than astemizole, cetirizine and loratadine.

Example 3

Activity of Topical Alcaftadine in Allergic Conjunctivitis

Alcaftadine has been shown to prevent signs and symptoms of allergic conjunctivitis in a murine model of active anaphylaxis.

Male SWR/J mice (The Jackson Laboratory, Bar Harbor, Me.), aged 5-7 weeks and weighing between 12.55 and 17.73 grams, were sensitized with a 100 µl dose of a suspension of 50 µg short ragweed allergen (Greer Labs, Inc., Lenoir, N.C.) and 1 mg of aluminum hydroxide (Fisher Scientific, Pittsburgh, Pa.) by intraperitoneal injection at two weeks and prior to treatment and challenge.

On Day 14, the mice were first given baseline exams to ensure that they did not present with significant irritation prior to treatment administration and challenge. The mice were then dosed topically in the eye with an alcaftadine 0.0625% ophthalmic solution, positive control (ophthalmic solution comprising combination of ketotifen 0.05% and pheniramine 0.5%), or placebo prior to an ocular challenge with 1.5 mg short ragweed allergen in phosphate buffered saline.

Fifteen (15) minutes after allergen challenge, mice were evaluated for clinical signs of allergic conjunctivitis by scoring for conjunctival redness, chemosis, tearing, and lid edema. Severity of clinical signs was scored by a trained technician using a standardized 0-2 scale. Alcaftadine was more effective than the positive control in preventing itching, redness, chemosis and lid edema. alcaftadine was as effective as the positive control and more effective than placebo in preventing tearing.

Example 4

Effects of Alcaftadine Ophthalmic Solution in Humans

The anti-allergic effect of a single dose of each of the three concentrations of alcaftadine ophthalmic solutions from Example 1 was assessed in a Conjunctival Allergen Challenge ("CAC") performed on adult volunteers with a history of allergic conjunctivitis. Subjects were selected after two visits to confirm reactivity to the allergen challenge. Subjects qualified for the study if they had a positive skin test and ocular reaction to at least one of several common allergens such as cat hair, cat dander, tree pollen, grass pollen, and the like. Subjects were then challenged with allergen by instilling reconstituted commercially available allergen into each eye on two separate visits 16 hours and 15 minutes after the bilateral instillation of alcaftadine, PATANOL® olopatadine hydrochloride ophthalmic solution 0.1% (Alcon, Inc., Fort Worth, Tex.) or vehicle, and the clinical response assessed.

Prevention of Ocular Itching

Patients administered alcaftadine 16 hours prior to challenge exhibited a dose-related inhibition of ocular itching. All concentrations of alcaftadine showed lower mean itching scores based on subject evaluation using a 5 point scale (i.e., less itching) than vehicle or PATANOL® at 3, 5 and 7 minutes post-challenge. When challenged 15 minutes post-treatment, the alcaftadine-treated subjects exhibited a dose-related inhibition of ocular itching as compared to placebo, and the 0.25% treatment group had lower itching scores than vehicle or PATANOL®.

Prevention of Conjunctival Redness

Patients administered alcaftadine 16 hours prior to challenge also exhibited a dose-related inhibition of conjunctival redness. Assessments were made at 7, 15 and 20 minutes post challenge based on investigator evaluations of redness using a 5 point scale. All concentrations of alcaftadine showed various degrees of reduction in mean conjunctival redness scores at most assessment times. When challenged at 15 minutes post-treatment, the 0.25% treatment group had lower scores than vehicle or PATANOL®.

Prevention of Nasal Symptoms

Similar results were observed for the prevention of nasal symptoms induced by CAC. Nasal symptoms of sneezing, rhinorrhea, pruritis (nasal and ear/palate) and nasal congestion were assessed by subjects using standardized scales.

All concentrations of alcaftadine showed some degree of relief of nasal congestion and rhinorrhea at various time points. These numbers often reached statistical significance versus either placebo and in some instances active control (p≤0.05). Similar results were demonstrated for the parameters of itching in the nose, palate and ear. No effect on sneezing was demonstrated in this study; however, baseline sneezing incidence (pre-treatment) was likely too low to detect a therapeutic effect if one existed. In summary, significant reduction of rhinorrhea, nasal congestion, and pruritis of the palate/ear were seen at majority of timepoints at both onset and duration visits.

Example 5

Effect of Sterilization with Gamma Irradiation

Alcaftadine is susceptible to oxidation and the primary degradation product has been identified as the N-oxide structure below. The existence of the N-oxide structures as the primary oxidative degradation peak was confirmed as having the same HPLC relative retention time as a synthetically produced N-oxide structures and also confirmed using mass spectroscopy.

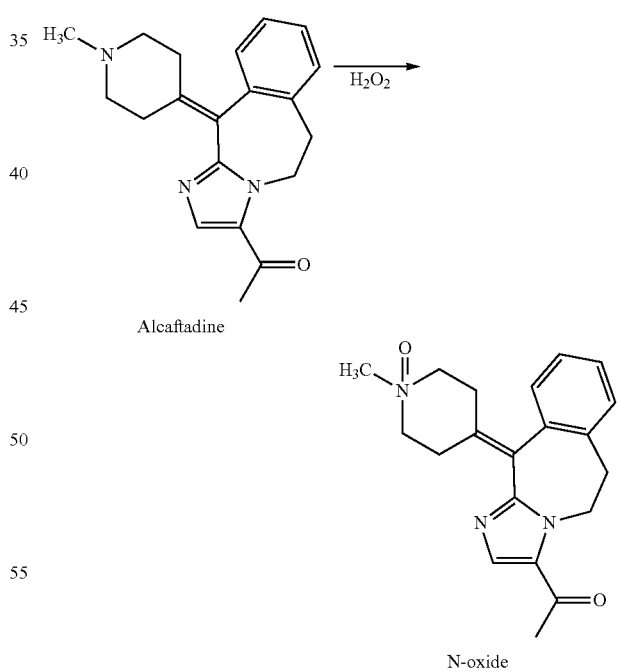

To investigate the effects of the gamma irradiation process used to sterilize the LDPE bottles, the chemical stability of alcaftadine was studied using different lots of bottles, either gamma irradiated or non-sterilized.

Materials and Methods:
The following materials were used in this study.
2.5 mg/ml alfactadine solution Non-sterilized 5 ml LDPE bottles (DUPONT 20-6064) from Bunder Glas GmbH (Germany)

Non-sterilized 5 ml LDPE bottles (DUPONT 20-6064) from Rexam (France)

Sterilized (gamma irradiated at 25 kGy) LDPE bottles (DUPONT 20-6064) from Bunder Glas GmbH Scintillation vials—20 ml clear glass with Teflon coated cap Millex GV syringe filter unit Results:

Chemical stability results for alcaftadine solution stored in either non-sterilized bottles (Rexam or Bunder Glas) or gamma-irradiated bottles (Bunder Glas) are summarized in Table 2. All samples were assayed by HPLC after 6 and 14 days of storage at 50° C. Light exposure was not controlled during storage. The solution was stored in either Rexam bottles (without sterilization), Bunder Glas bottles (sterilized with y Irradiation or without sterilization) and in glass vials.

TABLE 2

| Container Description | Sterilization Process | Storage Condition | Time (days) | Alcaftadine (mg/mL) | Oxide (%) |
|---|---|---|---|---|---|
| Initial Solution | N/A | N/A | N/A | 2.47 | 0.02 |
| Glass Vials | N/A | 5° C. | 6 | 2.52 | 0.008 |
| Glass Vials | N/A | 50° C. | 6 | 2.57* | 0.024 |
| Rexam | None | 50° C. | 6 | 2.46 | 0.015 |
|  |  |  | 14 | 2.48 | 0.033 |
| Bunder Glas | None | 50° C. | 6 | 2.48 | 0.018 |
|  |  |  | 14 | 2.48 | 0.042 |
| Bunder Glas | Y Irradiation | 50° C. | 6 | 2.41 | 0.199 |
|  |  |  | 14 | 2.39 | 0.202 |

*Sample showed significant evaporation, consistent with the higher assay value observed Conclusions:

Alcaftadine stored in gamma irradiated Bunder Glas bottles showed significantly increased levels of N-oxide formation compared with glass vials and non-sterilized Rexam and Bunder Glas bottles. This data suggests that the gamma irradiation sterilization process may be the primary cause of oxidation by inducing chemical or physical changes in the polyethylene bottle.

Example 6

Effect of Sterilization with Ethylene Oxide

Both non-sterilized Rexam and Bunder Glas bottles were sterilized using ethylene oxide. Stability studies were initiated and ethylene oxide levels determined to be <1 ppm (under ambient conditions) using a water extraction test method (ANSI/AAMI/ISO: 10993-7) by AppTec (Marietta, Ga.).

Materials and Methods:

The 2.5 mg/ml alcaftadine solution was used in this study. Bottles were sterilized using ethylene oxide in accordance with the protocol set forth in Table 3:

TABLE 3

| Phase | Parameter | Set-point |
|---|---|---|
| PRECONDITIONING | Temperature | 40° C. |
|  | % Rel. Humidity | 60% |
|  | Time | ≥16 hours |
|  | Transfer time → sterilizer | 45 minutes |
| ETO processing | Temperature | 45° C. |
| Initial vacuum | Pressure | 70 mbarA |

TABLE 3-continued

| Phase | Parameter | Set-point |
|---|---|---|
| Steam injection | Pressure | 42 mbars |
| Steam dwell | Time | 45 minutes |
| ETO exposure | Nitrogen injection | 250 mbarA |
|  | ETO injection | 744 mbarA |
|  | Gas dwell time | 3 Hours |
|  | ETO concentration | 800 ± 50 mg/l |
| Gas removal | (calculated) | 75 mbarA |
| 2 nitrogen washes | Pressure | 75 → 500 → 75 mbarA |
| 1 air wash | Pressure | 75 → 500 → 75 mbarA |
|  | Pressure |  |
| Aeration | Temperature | 40° C. |
|  | Time | 10 days |

Results:

The chemical stability results for alcaftadine stored in ethylene oxide sterilized Rexam and Bunder Glas bottles are summarized in Table 4.

TABLE 4

| Container Description | Sterilization Process | Time (days) at 50° C. | Alcaftadine (mg/ml) | N-Oxide (%) |
|---|---|---|---|---|
| Glass Vials | N/A | 5 | 2.48 | 0.022 |
|  |  | 14 | 2.51 | 0.028 |
| Bunder Glas | Ethylene Oxide | 5 | 2.46 | 0.052 |
|  |  | 14 | 2.48 | 0.074 |
| Rexam | Ethylene Oxide | 5 | 2.50 | 0.018 |
|  |  | 14 | 2.58 | 0.025 |

Conclusions:

Based on 14 days of storage at 50° C. under ambient light conditions, alfactadine has significantly lower N-oxide levels in ethylene oxide sterilized Bunder Glas bottles than gamma irradiated bottles. In this study, the amount of N-oxide formation in Rexam bottles is similar to that observed in the glass vials (0.025% and 0.028%, respectively) and slightly higher in the Bunder Glas bottles (0.074%) after 14 days of storage at 50° C.

Example 7

Effect of Alcaftadine on Mast Cell Degranulation

The cell stabilization potential of alcaftadine was evaluated using the RBL-CCR1 (Rat Basophil Leukemia-Chemokine Receptor-1) cell line as a way of investigating its ability to effect mast cell stabilization. The use of basophil cell lines to assess anti-allergic drugs for cell stabilization potential is well established. Physiologically, basophils are similar to mast cells, containing pre-formed inflammatory mediators that are released through a similar degranulation process involving IgE cross-linking. Because these cell lines are readily available, they present efficiencies over conducting stabilization assays in mast cell lines.

Cultured RBL-CCR1 cells were sensitized to anti-DNP IgE. Following sensitization, cells were treated with various concentrations of alcaftadine or its major active metabolite (0.083%, 0.0083% and 0.00083%) or ophthalmic vehicle (placebo), and stimulated with DNP and/or MIP-1a (Macrophage Inflammatory Protein-1 alpha, a degranulation enhancer) to induce degranulation. A 10× and 100× placebo control solution (ophthalmic vehicle solution) in D-DEM (Dulbecco's modified Eagle's medium) was also employed.

Stimulation with DNP-HSA (2,4-Dinitrophenyl hapten conjugated to Human Serum Albumin) alone and MIP-1a alone did not induce significant levels of degranulation.

However, co-stimulation induced a robust degranulation response. With all three degranulation stimuli, (DNP-HAS alone, MIP-1a alone, and co-stimulation) the highest concentration of parent drug, metabolite, and placebo caused unanticipated and significant degranulation, In the co-stimulation assay, alcaftadine concentrations of 0.0083% and 0.00083% were superior at cell stabilization compared to co-stimulation control and negative controls (placebo 10× [vehicle 3.3% in D-MEM] and placebo 100× [vehicle 0.33% in D-MEM] respectively). This superiority was statistically significant (p<0.0001 for both concentrations). Treatment with 6,11-dihydro-11-(1-methyl-4-piperdinylidene)-5H-imidazo[2,1-b][3]benazepine-3-carboxylic acid (CAS #147083-93-0) at concentrations of 0.0083% and 0.00083% was also superior at cell stabilization compared to co-stimulation control and negative controls (placebo 10× and placebo 100×, respectively). Again, statistical significance was achieved (p<0.0001 for both concentrations). Treatment with placebo 10× alone also indicated some stabilization compared to the co-stimulation control and the effect was statistically significant (p<0.05).

The addition of the alcaftadine or 6,11-dihydro-11-(1-methyl-4-piperdinylidene)-5H-imidazo[2,1-b][3]benazepine-3-carboxylic acid (CAS #147083-93-0) enhanced the stabilization effect at the 10× dose level, demonstrating the positive effect of the test agents at membrane stabilization. Stabilization was not observed at the 100× dilution level. Overall, the results of this study suggest the alcaftadine and 6,11-dihydro-11-(1-methyl-4-piperdinylidene)-5H-imidazo[2,1-b][3]benazepine-3-carboxylic acid (CAS #147083-93-0) are effective membrane stabilizing agents.

Example 8

Effect of Alcaftadine on Human $H_4$ Receptor

The pharmacological activity of alcaftadine or 6,11-dihydro-11-(1-methyl-4-piperdinylidene)-5H-imidazo[2,1-b][3]benazepine-3-carboxylic acid (CAS #147083-93-0) on the human histamine $H_4$ receptor ($H_4R$) was investigated. The $H_4R$ is the fourth histamine receptor that has been identified and it appears to be primarily expressed on eosinophils, T cells, dendritic cells, basophils and mast cells, cell types intimately involved with development and perpetuation of allergic responses. $H_4R$ has been shown to mediate mast cell, eosinophil and dendritic cell chemotaxis and can effect cytokine production from dendritic cells and T cells. Antagonists for the receptor are clearly anti-inflammatory in vivo and are efficacious in animal models of asthma and colitis. Alcaftadine and 6,11-dihydro-11-(1-methyl-4-piperdinylidene)-5H-imidazo[2,1-b][3]benazepine-3-carboxylic acid (CAS #147083-93-0) were tested using cells transfected with the receptor for binding to the $H_4R$ and for an indication as to whether they were agonists or antagonists of the receptor.

Alcaftadine and 6,11-dihydro-11-(1-methyl-4-piperdinylidene)-5H-imidazo[2,1-b][3]benazepine-3-carboxylic acid (CAS #147083-93-0) were prepared at 10 mM in 100% dimethylsulfoxide (DMSO) for the binding assays and at 10 mM in Na/K phosphate buffer, pH 7.0, for the cellular assays. Cell pellets from SK-N-MC cells transfected with human $H_4$ receptor were homogenized in 20 mM Tris-HCl/0.5 mM ethylendediaminetetraacetic acid (EDTA) pH 8.0 (TE buffer). Supernatants collected after centrifugation at 800 g were recentrifuged at 30,000 g for 30 min. Pellets were re-homogenized in TE buffer. For competition binding studies, membranes were incubated with 10 nM [$^3$H]histamine with or without test compounds for 45 min at 25° C. Non-specific binding was defined with 100 μM cold histamine. Ki values were calculated based on an experimentally determined $K_d$ value of 5 nM for [$^3$H]histamine and a ligand concentration of 10 nM according to Cheng and Prusoff. Seven concentrations of compound were tested spanning $10^{-11}$ to $10^{-5}$ M with each concentration being run in triplicate. The triplicates were averaged and an $IC_{50}$ (50% inhibitory concentration) curve was generated. This assay was run twice and the results are reported as the average of the two runs. SK-N-MC cell lines were created that express a reporter gene construct and the human $H_4$ receptor full-coding region. The reporter gene was .beta.-galactosidase under the control of cyclic adenosine monophosphate (cAMP) responsive elements. Cells were plated in 96-well plates the night before the assay. Antagonists were added 10 min prior to the addition of histamine, which was added directly to the cell medium. Forskolin (5 μM final concentration) was added 10 min after the addition of histamine. Cells were returned to the incubator for 6 h at 37° C. The medium was then aspirated and cells were lysed with 25 μL of 0.1× assay buffer (10 mM sodium phosphate, pH 8, 0.2 mM $MgSO_4$, 0.01 mM $MnCl_2$) and incubated at room temperature for 10 min. Cells were then incubated for 10 min with 100 μL of 1× assay buffer containing 0.5% Triton and 40 mM β-mercaptoethanol. Color was developed using 25 μL of 1 mg/mL substrate solution (chlorophenol red β-D-galactopyranoside; Roche Molecular Biochemicals, Indianapolis, Ind.). Color was quantitated on a microplate reader at absorbance 570 nm. For agonist determination a titration of compounds from $10^{-11}$ to $10^{-4}$ M in duplicate were added in the absence of histamine. The values for the duplicates were averaged and used to calculate the $EC_{50}$ (effective concentration 50) for the inhibition of cyclic AMP production by forskolin. This assay was repeated three times. For antagonist determination a titration of histamine from $10^{-10}$ to $10^{-3}$ M was run in duplicate in the presence of 1.2, 3.7, 11, 33, and 100 μM compound. The duplicates were averaged and the $EC_{50}$ for histamine at each of the different concentrations of compound were used for a Schild plot to derived the $pA_2$ values, which are the negative log of the concentration of compound needed to shift the histamine $EC_{50}$ by 2-fold.

The alcaftadine and 6,11-dihydro-11-(1-methyl-4-piperdinylidene)-5H-imidazo[2,1-b][3]benazepine-3-carboxylic acid (CAS #147083-93-0) were tested for their ability to displace [$^3$H]-histamine binding to membranes from SK-N-MC cells stably transfected with histamine $H_4$ receptor. Competition with [$^3$H]-histamine indicates that the compounds can bind to the receptor. The binding curves showed that alcaftadine binds to the receptor with an average $K_i$ value of 2.9 μM, whereas 6,11-dihydro-11-(1-methyl-4-piperdinylidene)-5H-imidazo[2,1-b][3]benazepine-3-carboxylic acid (CAS #147083-93-0) does not bind to the receptor at concentrations up to 10 μM.

To test whether alcaftadine or 6,11-dihydro-11-(1-methyl-4-piperdinylidene)-5H-imidazo[2,1-b][3]benazepine-3-carboxylic acid (CAS #147083-93-0) were $H_4$ receptor agonists, functional assays were carried out in SK-N-MC cells transfected with the human histamine $H_4$ receptor. The ability of the compounds to inhibit forskolin-induced cAMP increases was assessed. The results showed that histamine is an agonist of the receptor and causes a dose-dependent inhibition of forskolin-induced cAMP levels. However, neither alcaftadine or 6,11-dihydro-11-(1-methyl-4-piperdinylidene)-5H-imidazo[2,1-b][3]benazepine-3-carboxylic acid (CAS #147083-93-0) showed any inhibition of cAMP levels and therefore neither is an agonist of the $H_4$ receptor at concentrations up to 100 µM.

To test whether alcaftadine or 6,11-dihydro-11-(1-methyl-4-piperdinylidene)-5H-imidazo[2,1-b][3]benzazepine-3-carboxylic acid (CAS #147083-93-0) were antagonists of the $H_4$ receptor, the ability of the compounds shift the $EC_{50}$ of the histamine inhibition of forskolin-induced cAMP increases was assessed in SK-N-MC cells transfected with the human histamine $H_4$ receptor. The results showed that increasing concentrations of alcaftadine caused parallel and rightward shifts in the histamine (HA) dose response curves leading to an increase in the $EC_{50}$ for histamine modulation of the $H_4$ receptor. This effect indicates that alcaftadine is a competitive antagonist of the receptor. The x-intercept of the Schild plot gives a $pA_2$ value of 5.6, which represents the negative log of the concentration of antagonist need to induce a 2-fold shift in the histamine $EC_{50}$. Theoretically the $pA_2$ value should be equal to the $pK_i$, which is indeed observed (5.6 versus 5.5). Alcaftadine or 6,11-dihydro-11-(1-methyl-4-piperdinylidene)-5H-imidazo[2,1-b][3]benzazepine-3-carboxylic acid (CAS #147083-93-0) did not cause any shift at concentrations up to 100 µM, which is consistent with its inability to bind to the receptor.

These results indicate that alcaftadine binds to the $H_4$ receptor with an average $K_i$ value of 2.9 µM. Neither alcaftadine or 6,11-dihydro-11-(1-methyl-4-piperdinylidene)-5H-imidazo[2,1-b][3]benzazepine-3-carboxylic acid (CAS #147083-93-0) is an agonist of the $H_4$ receptor at concentrations up to 100 µM. However, alcaftadine, but not alcaftadine or 6,11-dihydro-11-(1-methyl-4-piperdinylidene)-5H-imidazo[2,1-b][3]benzazepine-3-carboxylic acid (CAS #147083-93-0) (up to 100 µM), is an antagonist of the human histamine $H_4$ receptor with a $K_i$ value of 2.9 µM and $pA_2$ value of 5.6.

Example 9

Effects of Alcaftadine on the Integrity of Conjunctival Epithelium

To investigate the ability of alcaftadine to maintain the integrity of conjunctival epithelium, changes in the expression of the tight junction proteins ZO-1 and E-cadherin (an induction for E-cadherin and qualitative change-from focal to diffuse for ZO-1) were evaluated following specific conjunctival allergen challenge. These changes are associated with an increased permeability of the conjunctival and other epithelial tissues. This in vivo experiment examined what effect alcaftadine (topical administration 1 and 2 hours pre-challenge) had on the modulation of these proteins.

Mice were sensitized with short ragweed (SRW) in aluminum hydroxide via intraperitoneal administration (Day 0, 7, and 15) and eye drop instillation (Day 8 and 15). On Day 20, mice were further sensitized with eye drops containing only SRW. On Day 27, the mice were treated topically with either 5 µL alcaftadine or vehicle at 1 and 2 hours prior to challenge. SRW was instilled topically to both eyes. The expression of these proteins in naive eyes were also monitored. Changes in the expression of the tight junction proteins ZO-1 and E-cadherin were observed 1-hour post conjunctival allergen challenge with SRW. The proteins were detected using FITC-conjugated monoclonal antibodies specific for ZO-1 and E-cadherin and were visualized by confocal microscopy (Ziess). Naive eyes were from mice that had not been sensitized or challenged.

The naive (no challenge and no treatment) ZO-1 and E-cadherin proteins showed focal qualitative properties. However, comparing this to vehicle treated proteins, the vehicle treated proteins showed diffuse qualitative changes. The transition from focal to diffuse staining is associated with increased permeability of the epithelium. Comparing naive ZO-1 and E-cadherin proteins with alcaftadine-treated proteins, the results show minimal difference in qualitative properties. Images of ZO-1 and E-cadherin proteins showed no or minimal difference between naive (negative control) and alcaftadine treatment, while there was a clear and distinct difference with vehicle treatment.

These results suggest alcaftadine maintains the integrity of conjunctival epithelial tight junctions (typified by focal ZO-1 expression) and inhibits the induction of E-cadherin expression normally observed following specific conjunctival allergen challenge.

Example 10

Effect of Alcaftadine on Vascular Leakage and Cellular Infiltrates

Allergic inflammation can be separated into two distinct phases, the early phase and the late phase. The early phase inflammatory response occurs rapidly following mast cell degranulation and is characterized by vascular endothelial cell gaping and leakage (i.e. swelling) and itching. The late phase inflammatory response peaks approximately 24 hours after mast cell degranulation and is characterized by the appearance of cellular infiltrates (eosinophils and neutrophils). Both eosinophils and neutrophils are known to have a profound effect on exponentiating the late phase of the inflammatory response. Upon arriving at the site of inflammation, these cells release various peroxidases and other antimicrobial factors that function to kill off invading pathogens but, in the case of severe or chronic inflammation, damage surrounding tissues and cause further release of pro-inflammatory mediators.

Alcaftadine ophthalmic solution was evaluated to determine if topical treatment could reduce early phase and late phase allergic inflammation in a murine model of allergic conjunctivitis. Evans Blue Dye Leakage was used to assess the impact on vascular permeability during the early phase inflammatory response Conjunctiva was taken at 24 hours, stained, and assessed for presence of neutrophil and eosinophil infiltration to evaluate late phase anti-inflammatory activity.

All mice were sensitized with short ragweed (SRW) in aluminum hydroxide via intraperitoneal administration (Day 0, 7, and 14) and eye drop instillation (Day 8 and 15). On Day 20, mice were again sensitized with eye drops of SRW.

On Day 27, two topical administrations of the clinical dose of alcaftadine 2.5 mg/ml or vehicle were instilled at 1 and 2 hours pre-challenge. Alcaftadine and vehicle were administered topically at a 5 µL saturating dose as treatment arms based on a randomization code. The treatment arms were as follows:

1. Negative Control. Sensitized, No challenge, no treatment (negative control) (N=12)
2. Sensitized, Challenge, no treatment (positive control) (N=12)
3. Sensitized, Challenge, alcaftadine 2.5 mg/ml treatment (N=10)
4. Sensitized, Challenge, vehicle treatment (N=12)

Vascular leak was determined by means of Evans Blue Dye Extravasation following allergen challenge for N=6 animals except the alcaftadine treatment arm, where N=4 animals were sacrificed and tested (two animals died during the procedure). The treatment groups were compared using T-test and p<0.05 was considered to be statistically significant. Dissection was performed on the remaining animals, N=6 per treatment arm, 24 hours post-conjunctival allergen challenge (CAC) to assess eosinophil and neutrophil recruitment in the forniceal area. The tissues were processed either as frozen or plastic blocks prior to sectioning on a microtome. The numbers of eosinophils and neutrophils were determined both by light microscopy of Giemsa or H&E stained sections or by immunohistochemistry using cell specific monoclonal antibodies. The treatment groups were compared using T-test and p<0.05 was considered to be statistically significant.

There was no significant difference between the Negative Control (no challenge group—Group 1) and Challenged but untreated (Group 2) group. However, as expected, there was a numerical difference with Group 2 having higher scores of vascular leak. There was a significant difference between the vehicle treatment (Group 4) and alcaftadine treatment (Group 3) (p<0.05) groups with alcaftadine successfully preventing vascular leakage compared to vehicle. As expected, there was a significant difference between the negative control (no challenge group-Group 1) and untreated but challenged group (Group 2). Alcaftadine (Group 3) did not prevent eosinophil or neutrophil recruitment compared to controls.

Regarding vascular leakage, the typical induction of vascular leak was not observed in Group 2 (Challenged and untreated). However, alcaftadine did significantly inhibit vascular leak following CAC as compared to mice treated with vehicle alone. Based on observations from previous studies, the low level of vascular leak in Group 2 is atypical and is most likely due to experimental error associated with in vivo experiments. The decreased vascular leak in the alcaftadine treated animals is supportive of a therapeutic role for alcaftadine in this conjunctival allergen challenge model.

In the evaluation of eosinophil or neutrophil recruitment, the significant difference between the negative and positive controls suggests the model worked as expected. However, at the dose used, alcaftadine does not inhibit eosinophil or neutrophil recruitment in the late phase response, in the murine model of allergic conjunctivitis following allergen challenge in sensitized mice.

The results of this study indicate that alcaftadine did significantly inhibit vascular leak following conjunctival allergen challenge. However, it does not appear to inhibit eosinophil or neutrophil recruitment in the late phase response, in the murine model of allergic conjunctivitis following allergen challenge in sensitized mice.

Example 11

Systemic Levels of Alcaftadine in Patients

Patients were bilaterally dosed with 0.25% ophthalmic solutions of alcaftadine for seven days. The plasma levels of those patients was assessed pre-dose, and 0.25, 0.5, 1, 1.5, 2, 3, 4, 6, 8, 12, and 18 hour post medication instillation on days one and seven. Plasma concentrations of Alcaftadine reached $C_{max}$ rapidly and declined to below the lower limit of quantification (0.01 ng/mL) by 3 hours post dosing. Mean $C_{max}$ values (highest value measured at any time point) were quite low, mean of 0.051 ng/mL on Day 1 and 0.060 ng/mL on Day 7; the maximum plasma concentrations were less than 0.12 ng/mL for all subjects.

Example 12

Systemic Levels of 6,11-dihydro-11-(1-methyl-4-piperdinylidene)-5H-imidazo[2,1-b][3]benazepine-3-carboxylic acid in Patients Patients were bilaterally dosed with 0.25% ophthalmic solutions of 6,11-dihydro-11-(1-methyl-4-piperdinylidene)-5H-imidazo[2,1-b][3]benazepine-3-carboxylic acid for seven days. The plasma levels of those patients was assessed pre-dose, and 0.25, 0.5, 1, 1.5, 2, 3, 4, 6, 8, 12, and 18 hour post medication instillation on days one and seven. Plasma concentrations of 6,11-dihydro-11-(1-methyl-4-piperdinylidene)-5H-imidazo[2,1-b][3]benazepine-3-carboxylic acid reached $C_{max}$ rapidly and declined to below the lower limit of quantification (0.1 ng/mL) by 12 hours post dosing. Mean $C_{max}$ values of 3.228 ng/mL on Day 1 and 2.715 ng/mL on Day 7; the maximum plasma concentrations was 7.23 ng/mL.

The entire disclosure of each patent, patent application, and publication cited or described in this document is hereby incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. An ophthalmic composition, comprising: about 0.25% by weight of alcaftadine or its pharmaceutically acceptable salts.

2. The composition of claim 1, wherein the composition is in the form of a solution or suspension.

3. The composition of claim 2, wherein the pH of the composition ranges from about 6.5 to about 7.5.

4. The composition of claim 1, wherein the composition further comprises a pharmaceutically acceptable topical ophthalmic vehicle.

5. The composition of claim 4, wherein the composition when administered once daily to an eye of a human subject provides a therapeutically beneficial effect in treating at least one clinical symptom of ocular allergy.

6. The composition of claim 1, wherein the composition when administered once daily to an eye of a human subject provides a therapeutically beneficial effect in treating at least one clinical symptom of ocular allergy.

7. An ophthalmic composition, comprising: a pharmaceutically acceptable ophthalmic vehicle and 0.25% by weight of alcaftadine or a pharmaceutically acceptable salt, wherein the composition when administered once daily to an eye of a human subject provides a therapeutically beneficial effect in treating at least one clinical symptom of ocular allergy.

8. The composition of claim 7, wherein the pH of the composition ranges from about 6.5 to about 7.5.

9. A method of treating ocular allergy, the method comprising administering to the eye of a patient in need thereof an effective amount of an ophthalmic composition according to claim 1, wherein the administration treats at least one clinical symptom of ocular allergy.

10. The method of claim 9, wherein the ocular allergy is allergic conjunctivitis.

11. The method of claim 9, wherein the clinical symptom is a clinical symptom of ocular inflammation.

12. The method of claim 9, wherein the clinical symptom is ocular itching, ocular redness, swelling of the eyelids, chemosis, tearing, and nasal inflammation, nasal congestion, rhinorrhea, nasal pruritis, ear prurtis, palate prurtis, or sneezing.

13. The method of claim 9, for the treatment or prevention of at least two clinical symptoms.

14. The method of claim 13, wherein the at least two clinical symptoms are ocular itching and ocular redness.

15. The method of claim 9, for the treatment or prevention of at least three clinical symptoms.

16. The method of claim 15, wherein the at least three clinical symptoms are ocular itching, ocular redness, swelling of the eyelids, chemosis, and tearing.

17. The method of claim 9, wherein the clinical symptom is a mechanistic symptom associated with ocular allergy or ocular inflammation.

18. The method of claim 17, wherein the mechanistic symptom is vascular leakage, a reduction in the integrity of the conjunctival epithelial tight junctions, modulation of the $H_4$ receptor, or mast cell degradation.

19. The method of claim 9, wherein the clinical symptom is a nasal symptom of ocular allergy or ocular inflammation.

20. The method of claim 19, wherein the nasal symptom is nasal inflammation, nasal congestion, rhinorrhea, nasal pruritis, or sneezing.

\* \* \* \* \*